United States Patent [19]

Kawaguchi et al.

[11] Patent Number: 4,757,139

[45] Date of Patent: Jul. 12, 1988

[54] 5-FLUORO-2'-DEOXYURIDINE DERIVATIVE, PROCESSES FOR PREPARING SAME AND ANTITUMOR COMPOSITION CONTAINING THE SAME

[75] Inventors: Takeo Kawaguchi, Tokyo; Masahiko Saito, Saitama; Yoshiki Suzuki, Tokyo, all of Japan

[73] Assignee: Teijin Limited, Osaka, Japan

[21] Appl. No.: 717,275

[22] PCT Filed: Jul. 20, 1984

[86] PCT No.: PCT/JP84/00368

§ 371 Date: Mar. 20, 1985

§ 102(e) Date: Mar. 20, 1985

[87] PCT Pub. No.: WO85/00608

PCT Pub. Date: Feb. 14, 1985

[30] Foreign Application Priority Data

Jul. 20, 1983 [JP] Japan ................... 58-130756
Jan. 23, 1984 [JP] Japan ................... 59-8480

[51] Int. Cl.$^4$ .................. A61K 31/70; C07H 19/08
[52] U.S. Cl. .................. 536/23; 536/24; 536/26
[58] Field of Search .................. 536/23

[56] References Cited

U.S. PATENT DOCUMENTS 4,097,665 6/1978 Ishida et al. ................ 536/23
4,503,045 3/1985 Fujii et al. ................ 514/25

OTHER PUBLICATIONS

Kanzawa, F. et al., Cancer Chemother. Pharmacol., vol. 6(1), vol. 6, pp. 19–23, 1981.
Nishizawa, Y. et al., Biochemical Pharmacology, vol. 14, pp. 1605–1609, 1965.
Casida, J. et al., Biochemical Pharmacology, vol. 15, pp. 627–644, 1966.
Schwendener, R. A. et al., Biochem. Biophys. Res. Comm., vol. 126(2), pp. 660–666, 1985.
Kawaguchi, T. et al., Chem. Pharm. Bull., vol. 33(4), pp. 1652–1659, 1985.

*Primary Examiner*—J. R. Brown
*Assistant Examiner*—L. Eric Crane
*Attorney, Agent, or Firm*—Sughrue, Mion, Zinn, Macpeak, and Seas

[57] ABSTRACT

A 5-fluoro-2'-deoxyuridine derivative expressed by the following formula

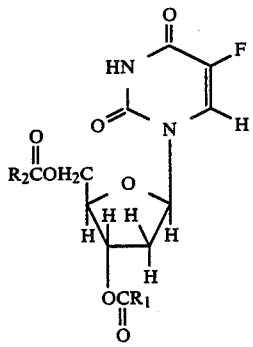

wherein $R_1$ and $R_2$ are the same or different from each other, each representing an alkyl group of 1 to 18 carbon atoms having a carboxyl group as a substituent, or an alkyl group of 9 to 14 carbon atoms, or its pharmacologically acceptable salt as the active ingredient.

Said 5-fluoro-2'-deoxyuridine derivative displays a high-level antitumor effect in low doses and shows outstanding safety.

1 Claim, No Drawings

5-FLUORO-2'-DEOXYURIDINE DERIVATIVE, PROCESSES FOR PREPARING SAME AND ANTITUMOR COMPOSITION CONTAINING THE SAME

TECHNICAL FIELD

The present invention relates to an antitumor composition. More particularly, this invention relates to an antitumor composition comprising, as its effective ingredient, a 5-floro-2'-deoxyuridine derivative which shows strong antitumor activity even in low doses, provides a very wide margin of safety and displays the highly sustained releasing effect in vivo for 5-fluoro-2'-deoxyuridine.

BACKGROUND ART

5-Fluorouracil is known as the compound having antitumor activity and to speak of its mode of action, it takes in vivo a metabolic pathway to 5-fluorouridinemonophosphate, then to 5-fluorouridinediphosphate, and further to 5-fluoro-2'-deoxyuridinemonophosphate, which inhibits thymidylate synthetase activity, thus providing the antitumor effect. Said 5-fluoro-2'-deoxyuridinemonophosphate is metabolizable further into 5-fluoro-2'-deoxyuridine.

The last-mentioned 5-fluoro-2'-deoxyuridine, one of said metabolites, is also known as the compound having an antitumor activity. However, it has been reported that, though 5-fluoro-2'-deoxyuridine shows a strong antitumor activity in vitro, it fails to exercise enough antitumor effect in experiments conducted in vivo on tumor-bearing animals (Cancer Research, 19, 494 (1959); Proc. Soc. Exp. Biol., N.Y., 97, 470 (1958); Proc. Soc. Exp. Biol., N.Y., 104, 127 (1960); Ann., N.Y. Acad. Sci., 76, 576 (1958)).

This is attributed to the fact that, in in vivo, the half-life period of 5-fluoro-2'-deoxyuridine is extremely short, so there is not enough time for 5-fluoro-2'-deoxyuridine to be in contact with the tumor cells (Cancer Research, 32, 1045 (1972); Clin. Pharmacol. Ther., 5, 581 (1964); Cancer Research, 38, 3479 (1978); Bull. Cancer (Paris), 66, 67 (1979); Bull. Cancer (Paris), 66, 75 (1979); Europ. J. Cancer, 16, 1087 (1980)).

Studies have hitherto been made by many specialists on 5-fluoro-2'-deoxyuridine in order to overcome the disadvantage mentioned above.

For example, 3-acyl-5-fluoro-2'-deoxyuridines (Japanese Patent Application Laid-open No. 163586/'79) and 3-acyl-3',5'-di-0-acetyl-5-fluoro-2'-deoxyuridines (Japanese Patent Application Laid-open Nos. 113797/'81 and 113795/'81) are known. These compounds, however, have not had their antitumor effect improved sufficiently enough and there is still a drawback in terms of their safety (therapeutic index).

It has also been reported that 3',5'-diacyl-5-fluoro-2'-deoxyuridines which have their 3'- and 5'-positions acylated with alkanoyl groups have antitumor activity (Biochemical Pharmacology, 14, 1605 (1965)). According to this report, 3',5'-diacyl-5-fluoro-2'-deoxyuridines have their antitumor activity tested always at doses ranging from 10 to 40 mg/kg/day, i.e., doses at which its parental compound 5-fluoro-2'-deoxyuridine showed antitumor activity. However, it has not yet been ascertained whether it has a significantly high level of antitumor activity and therapeutic index comparable to that of 5-fluoro-2'-deoxyuridine.

It is reported in the Cancer Chemother. Pharmacol., (1981) 6: 19~23, that, of the 3',5'-diacyl-5-fluoro-2'-deoxyuridine family whose 3'- and 5'-positions are acylated with an alkanoyl group, 3',5'-diacyl-5-fluoro-2'-deoxyuridine which has its 3'- and 5'-positions acylated with an acetyl ($C_2$), propanoyl ($C_3$), butyryl ($C_4$), hexanoyl ($C_6$), or palmitoyl ($C_{16}$) group exhibits an antitumor effect at a lower dose as compared with 5-fluoro-2'-deoxyuridine. With regard to the therapeutic index, however, these 3',5'-diacyl-5-fluoro-2'-deoxyuridines show an improvement by only 2 to 3 times that of 5-fluoro-2'-deoxyuridine.

DISCLOSURE OF THE INVENTION

The present invention provides an antitumor composition which comprises a 5-fluoro-2'-deoxyuridine derivative expressed by the following formula (I)

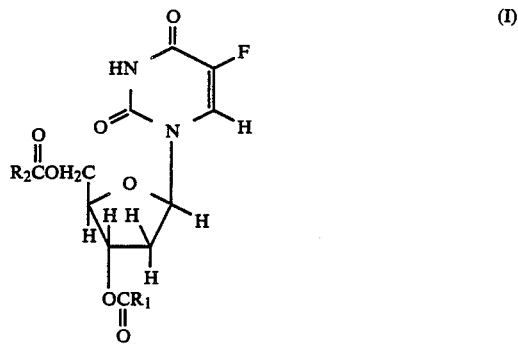

wherein $R_1$ and $R_2$ are the same or different from each other, each representing an alkyl group of 1 to 18 carbon atoms having a carboxyl group as a substituent, or an alkyl group of 9 to 14 carbon atoms, or their pharmacologically acceptable salts as the effective ingredient.

The 5-fluoro-2'-deoxyuridine derivative proposed by the present invention is a compound which shows strong antitimor activity even in low doses, provides a markedly improved therapeutic effect (therapeutic index), and displays the highly sustained releasing effect in vivo for 5-fluoro-2'-deoxyuridine. The compound, which comprises the 5-fluoro-2'-deoxyuridine derivatives of this invention in which $R^1$ and $R^2$ are an alkyl group of 1 to 18 carbon atoms having a carboxyl group as a substituent, is a novel compound.

BEST MODE OF CARRYING OUT THE INVENTION $R^1$ and $R^2$ of the 5-fluoro-2'-deoxyuridine derivative expressed by the aforementioned formula (I) of the present invention are the same or different from each other and represent an alkyl group of 1 to 18 carbon atoms having a carboxyl group as a substituent, or an alkyl group of 9 to 14 carbon atoms. As the alkyl group of 1 to 18 carbon atoms having a carboxyl group as substituent, there are straight chained or branched alkyl groups. Said carboxyl group may be substituted for a terminal carbon atom or any carbon atom other than a terminal carbon atom in the alkyl group. It is desirable for an alkyl group to have one carboxyl group substituted. As the alkyl group of 1 to 18 carbon atoms having a carboxyl group as the substituent, carboxymethyl, 2-carboxyethyl, 3-carboxypropyl, 4-carboxybutyl, 5-carboxypentyl, 6-carboxyhexyl, 7-carboxyheptyl, 8-carboxyoctyl, 9-carboxynonyl, 10-carboxydecyl, 11-carboxyundecyl, 12-carboxydodecyl, 13-carboxytridecyl, 14-carboxytetradecyl, 15-carboxypentadecyl, 16-carboxyhexadecyl, 17-carboxyheptadecyl, 18-carboxyoctaceyl, 3-carboxy-3-methylbutyl, 2-carboxydecyl, 2-carboxydodecyl, and 2-carboxytetradecyl, for instance, may be mentioned.

As the alkyl group of 9 to 14 carbon atoms, nonyl, decyl, undecyl, dodecyl, tridecyl, and tetradecyl, for instance, may be mentioned and nonyl, undecyl, and tridecyl are especially desirable.

The 5-fluoro-2'-deoxyuridine derivative of this invention can be used in the form of pharmacologically permissible salt. As the pharmacologically permissible salt, salts of carboxyl group may be usable in case where $R_1$ and $R_2$ are alkyl group of 1 to 18 carbon atoms having a carboxyl group as the substituent. As the salt of this type, such salts of alkali metals as sodium salt and potassium salt; such divalent or trivalent metal salts as calcium salt, magnesium salt, and aluminum salt; and such organic salts as ammonium salt, tetramethylammonium salt, monomethylammonium salt, dimethylammonium salt, trimethylammonium salt, morpholine salt, and piperidinium salt, for instance, may be mentioned.

As another pharmacologically permissible salt, acid addition salts with an acid added to the nitrogen atom at the 3-position may also be usable. As such an acid, such inorganic acids as hydrochloric acid, hydrobromic acid, sulfuric acid and phosphoric acid; such organic carboxylic acids as acetic acid, propionic acid, citric acid, succinic acid, tartaric acid, and maleic acid; and such organic sulfonic acids as methane-sulfonic acid, ethanesulfonic acid, benzenesulfonic acid, and p-toluenesulfonic acid, for instance, may be mentioned.

To give examples of the 5-fluoro-2'-deoxyuridine derivative, the following compounds may be mentioned:

3',5'-dimalonyl-5-fluoro-2'-deoxyuridine,
3',5'-disuccinyl-5-fluoro-2'-deoxyuridine,
3',5'-diglutaryl-5-fluoro-2'-deoxyuridine,
3',5'-diadipoyl-5-fluoro-2'-deoxyuridine,
3',5'-dipymeryl-5-fluoro-2'-deoxyuridine,
3',5'-disuberyl-5-fluoro-2'-deoxyuridine,
3',5'-disubesyl-5-fluoro-2'-deoxyuridine,
3',5'-didecanoyl-5-fluoro-2'-deoxyuridine,
3',5'-didodecanoyl-5-fluoro-2'-deoxyuridine,
3',5'-ditetradecanoyl-5-fluoro-2'-deoxyuridine.

The 5-fluoro-2'-deoxyuridine derivative of formula (I) prepared according to the present invention shows an excellent effect of prolonging the life span of a tumor bearing mouse upon administration in low dose ranging from 1/10 to 1/130 of the dose required for 5-fluoro-2'-deoxyuridine to show the similar degree of antitumor effect on prolonging the life span of the mouse bearing L1210 mouse leukemia cells. It has also been made clear that its therapeutic index, which shows the therapeutic advantage quantitatively, and is determined by dividing the dose required to obtain the maximum survival time of the L1210 bearing mouse (TLS max) by the dose required to increase the survival time by 30% ($ILS_{30}$), is 5 to 20 times higher than that of its parent compound, 5-fluoro-2'-deoxyuridine.

It has further been clarified that the 5-fluoro-2'-deoxyuridine derivative of this invention shows sustained release of 5-fluoro-2'-deoxyuridine by enzymatic reaction which takes place in the system of porcine liver esterase, etc. in vitro.

The foregoing facts substantiate a claim that the compound of this invention has a high antitumor effect because the 5-fluoro-2'-deoxyuridine derivative prepared according to this invention effects a sustained release of 5-fluoro-2'-deoxyuridine whose half life in vivo is very short and keeps it in contact with the tumor cells for a long period of time in the living body.

As mentioned above, the 5-fluoro-2'-deoxyuridine derivative of the present invention has an excellent antitumor effect, and accordingly an antitumor drug which comprises the 5-fluoro-2'-deoxyuridine derivative expressed by the aforementioned formula (I) as the effective ingredient can be provided according to the present invention.

The 5-fluoro-2'-deoxyuridine derivative of the present invention can be administered orally or parenterally such as subcutaneously, intramuscularly, intravenously, percutaneously, and rectally. Of these methods, oral and intravenous administrations are most advisable. As the dosage form for oral administration, tablets, pills, granules, powders, liquid preparations, suspensions, emulsions, liposome preparations, and capsules may be mentioned.

The preparation of tablets can be achieved according to any ordinary methods of forming tablets by use of such excipients as lactose, starch, crystalline cellulose, and hydroxypropyl cellulose; such binders as carboxymethyl cellulose, methyl cellulose, polyvinyl pyrrolidone, and sodium alginate; and such disintegrators as calcium carboxymethyl cellulose and starch. Pills, powders, granules, etc. can also be formed according to the ordinary method by use of such excepients, etc. as mentioned above. Emulsions and suspensions can be prepared according to the ordinary method by use of such glycerin esters as tricapyrtin, triacetin, and trilaurin; such vegetable oil a coconuts oil and fractionated coconuts oil; and such alcohols as ethanol. In preparing capsules, hard gelatin capsules may be filled with granule or powder and soft gelatin capsules may be filled with a liquid preparation.

As the form of dosage to be administered subcutaneously, intramuscularly or intravenously, there are injections prepared in the form of aqueous or nonaqueous solutions, suspensions, emulsions, and liposome preparations. In preparing nonaqueous solutions and suspensions, propylene glcyol, polyethylene glycol, olive oil, and ethyl oleate, for instance, are used and antiseptics and stabilizers are further added, if necessary. In the case of preparing aqueous solutions, such surfactants as polyoxyethylene hardened castor oil, polyoxyethylene sorbitan monolaurate, polyoxyethylene hardened castor oil, polysorbate 20, polysorbate 80, and polyoxyethylene sorbitan monooleate may be added as the solubilizing agent. As the lipid to be used for preparing emulsions and liposome preparations, vegetable oils, lecithin, phosphatidyl ethanolamine, phosphatidyl inositol, phosphatidyl serine, sphingomyelin, and phosphatidic acid cholesterol may be mentioned. As the stabilizer to be used for preparing emulsions and liposome preparations, dextran, albumin, vinyl polymer, monionic surfactant, gelatin, and hydroxyethyl starch may be used. Injections are usually sterilized by subjecting them to filtration through a bacterial filter or by treating them with a bactericide.

The dosage form for percutaneous administration includes, for instance, ointments and creams. Ointments are prepared according to ordinary methods by use of such fatty oils as castor oil and olive oil, and vaseline. Creams are prepared according to ordinary methods by use of fatty oil or such emulsifying agents as ethylene glycol and monosorbitan fatty acid esters.

For rectal administration, gelatin soft capsules and suppositories prepared by use of cacao butter are used.

The dose of the 5-fluoro-2'-deoxyuridine derivative of this invention varies depending upon the age and sex of a patient, the condition and nature of a disease, and the dosage form; however, the usual dose is 0.005 to 9 mg/kg/day, preferably 0.01 to 4 mg/kg/day.

The amount of the 5-fluoro-2'-deoxyuridine derivative to be contained in the antitumor composition of the present invention is determined in consideration of said dose. For example, the usual dose in the form of a tablets, capsules, injections, etc. shall contain 0.1 to 180 mg, preferably 0.2 to 80 mg, of the 5-fluoro-2'-deoxyuridine derivative.

The 5-fluoro-2'-deoxyuridine derivative of this invention can be given to a patient in dosage of more than one kind of them in combination.

In case where $R_1$ and $R_2$ of the 5-fluoro-2'-deoxyuridine derivatives expressed by formula (I) of this invention are alkyl group of 9 to 14 carbon atoms, such compounds can all be made synthetically according to any publicly known methods as shown, for instance, in the Biochemical Pharmacology, 14, 1605 (1965).

To give an example, they can be synthesized according to the ordinary method wherein 5-fluoro-2'-deoxyuridine is made to react with its corresponding acid halide or acid anhydride in the presence of such organic base as pyridine and trialkylamine.

The 5-fluoro-2'-deoxyuridine derivatives of this invention whose $R_1$ and $R_2$ are alkyl groups of 9, 11, and 13 carbon atoms respectively are disclosed in the Biochemical Pharmacology, 14, 1605 (1965) and are publicly known compounds.

In the case where $R_1$ and $R_2$ of the 5-fluoro-2'-deoxyuridine derivative expressed by formula (I) of this invention are respectively alkyl group of 1 to 18 carbon atoms having a carboxyl group as the substituent, namely the 5-fluoro-2'-deoxyuridine derivative expressed by the following formula (I')

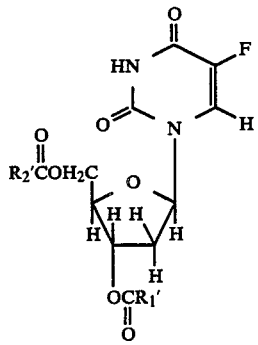

(I')

wherein $R_1'$ and $R_2'$ are the same or different from each other, each representing an alkyl group of 1 to 18 carbon atoms having a carboxyl group as a substituent, or their pharmaceutically acceptable salts, they are novel compounds.

These compounds can be synthesized according to the following methods.

(1) In the case where $R_1'$ and $R_2'$ are the same:

In the case where $R_1'$ and $R_2'$ are the same, the 5-fluoro-2'-deoxyuridine expressed by the following formula (I'-a)

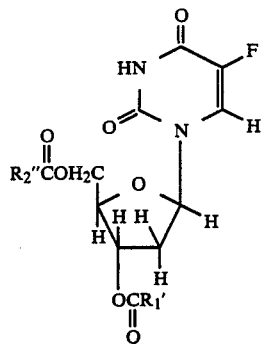

(I'-a)

wherein $R_1'$ and $R_2''$ are the same, representing an alkyl group of 1 to 18 carbon atoms having a carboxyl group as a substituent, can be prepared by allowing 5-fluoro-2'-deoxyuridine to react with carboxylic acid expressed by the following formula (II)

$$R_1'COOH \qquad (II)$$

wherein $R_1'$ is as defined hereinabove, or its reactive derivative in the presence of base.

As the reactive derivative of carboxylic acid of formula (II), such corresponding acid halides as acid chloride and acid bromide, acid anhydride, mixed acid anhydride, activated ester, and activated acid amide may be mentioned. Such acid halides as acid chloride and acid bromide are especially preferable of all.

As the base to be used in the reaction between carboxylic acid or its reactive derivative and 5-fluoro-2'-deoxyuridine, such organic bases as trimethylamine, triethylamine, tributylamine, pyridine, N-methylmorpholine, 2,6-lutidine, and N,N-dimethylaminopyridine; and such inorganic bases as alkali acetates and alkali carbonates may be mentioned. Of these bases, such organic bases as pyridine and triethylamine ae preferable. As the reaction solvent, nonpolar solvents including such ethers as ethyl ether, tetrahydrofuran, and dioxane; such hydrocarbon halogenides as methylene chloride and carbon tetrachloride; and such aromatic hydrocarbons as benzene and toluene may be among desirable solvents. To speak of the amounts of the respective species to be used in the reaction, it is necessary to use more than two molar equivalents of carboxylic acid expressed by formula (II) or its relative derivative against 5-fluoro-2'-deoxyuridine. The base is also used in more than two molar equivalents. It is advisable to carry out on the reaction with cooling by use of ice in the initial stage and, thereafter, to carry out the reaction at room temperature. The reaction times varies depending upon the kind and quantity of the compounds to be used in the reaction, however, it is usually in the range of 1 to 5 hours.

Though the 5-fluoro-2'-deoxyuridine derivative of this invention is thus obtained, it may further be subjected to the salt-forming reaction in order to obtain its pharmacologically permissible salt, if necessary. The salf-forming reaction is effected according to the ordinary method. To adduce an example, when any of sodium hydroxide, potassium hydroxide, sodium carbonate, ammonia, trimethylamine, monoethanolamine, and morpholine is made to react with the 5-fluoro-2'-deoxyuridine derivative for neutralization according to the ordinary method, the salt of a carboxyl group in the molecule of the 5-fluoro-2'-deoxyuridine derivative is obtained.

An acid addition salt of the 5-fluoro-2'-deoxyuridine derivative can be obtained by bringing the 5-fluoro-2'-deoxyuridine into contact with any of inorganic acids, organic carboxylic acids, and organic sulfonic acids in an organic solvent.

The isolation and purification of the desired compound after the reaction can be carried out according to the ordinary methods such as recrystallization, thin-layer chromatography, and column chromatography.

(2) In the case where $R_1'$ and $R_2'$ are different from each other:

In the case where $R_1'$ and $R_2'$ are different from each other, the 5-fluoro-2'-deoxyuridine derivative expressed by the following formula (I'-b)

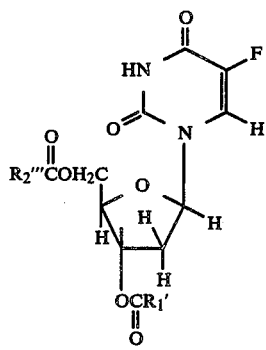

(I'-b)

wherein $R_1'$ and $R_2'''$ are different from each other, each representing an alkyl group of 1 to 18 carbon atoms having a carboxyl group as a substituent, can be synthesized by making the compound expressed by the following formula (III)

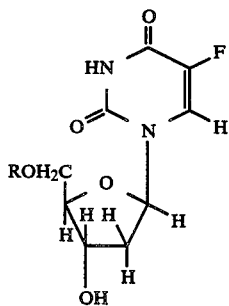

(III)

wherein R represents a protective group react with carboxylic acid expressed by the following formula (II)

$R_1'COOH$ (II)

wherein $R_1'$ is as defined hereinabove, or its reactive derivative in the presence of base. After the release of the protective group from the reaction product, the reaction product is allowed to react with carboxylic acid expressed by the following formula (IV)

$R_2'''COOH$ (IV)

wherein $R_2'''$ is as defined hereinabove or its reactive derivative in the presence of base, followed by the salt-forming reaction, if required so.

In the compound expressed by the aforementioned formula (III) to be used in the present invention, R indicates a protecting group. As the protecting group, the protecting groups like triphenylmethyl group and triphenylmethoxyacetyl group which have high steric hindrance performance may be mentioned. The compound of the aformentioned formula (III) can be prepared according to the ordinary method.

The reaction between the compound of formula (III) and carboxylic acid of formula (II) or its reactive derivative can be conducted according to the same method as mentioned above with an exception of making them react in amounts equimolar with each other.

The releasing of the protective group can be effected under the ordinary hydrolysis conditions in acidic or alkaline solutions; more particularly under the acidic conditions in aqueous solution of acetic acid or hydrochloric acid or under the alkaline conditions in ammoniac methanol solution.

After the release of the protective group, the reaction of the intermediate reaction product with carboxylic acid of formula (IV) or its reactive derivative can be carried out after the same method as mentioned above with an exception of using carboxylic acid of formula (IV) or its reactive derivative in equimolar amounts. The salt-forming reaction can also be effected in the same way as mentioned above.

The foregoing are the methods by which the 5-fluoro-2'-deoxyuridine derivative or its pharmacologically acceptable salt is prepared.

The following Examples illustrate the invention in detail.

EXAMPLE 1

Synthesis of 3',5'-diadipoyl-5-fluoro-2'-deoxyuridine

To a solution of 250 mg (1.01 mmol) of 5-fluoro-2'-deoxyuridine in 10 ml of anhydrous pyridine was added 800 mg (4.37 mmol) of adipoyl chloride for about 3 hours, and the mixture was stirred overnight at room temperature. The reaction mixture was then poured into 50 ml of ice-cold water and stirred for 1 hour. To the reaction mixture was added 2N HCl to adjust to pH 4.00, and the reaction product was extracted three times with 20 ml of ethyl acetate. Ethyl acetate was distilled away at room temperature under reduced pressure and the obtained crude product was dissolved in chloroform. The solution was purified by column chromatography on silica gel. The chloroform-ethanol (95:5 to 90:10) eluants were collected and concentrated to yield 3',5'-diadipoyl-5-fluoro-2'-deoxyuridine. The yield was 40%.

UV($\lambda$max): 209 nm, 268 nm

NMR($\delta_{CDCl_3}{}^{TMS}$—$D_3COD$): 1.5–1.8 (m, 8H), 2.1–2.5 (m, 10H), 4.2–4.4 (m, 3H), 5.1–5.3 (m, 1H), 6.3 (t, 1H), 7.9 (d, 1H, J=6.5 Hz).

m.p.: 44°–45° C.

EXAMPLE 2

Synthesis of 3',5'-diglutaryl-5-fluoro-2'-deoxyuridine

To a solution of 220 mg (0.89 mmole) of 5-fluoro-2'-deoxyuridine in 3 ml of anhydrous pyridine was added 280 mg (2.46 mmole) of glutaric anhydride. The mixture was stirred overnight at room temperature and for another 3 hours at 80° C. The reaction mixture was poured into 30 ml of ice-cold water and stirred for 1 hour. To the reaction mixture was added 2N HCl to adjust to pH 4.00 and the reaction product was extracted three times with 15 ml of ethyl acetate. Ethyl acetate was distilled off at room temperature under reduced pressure to obtain the crude product. The crude product was dissolved in chloroform and purified by column chromatography on silica gel. The chloroform-ethanol (93:7 to 98:12) eluants were collected and concentrated to obtain oily 3',5'-diglutaryl-5-fluoro-2'-deoxyuridine. The yield was 70%.

UV(λmax): 209 nm, 268 nm

NMR($\delta_{D3COD}^{TMS}$): 1.7–2.2 (m, 4H), 2.2–2.7 (m, 10H), 4.2–4.5 (m, 3H), 5.2–5.4 (m, 1H), 6.25 (t, 1H), 7.92 (d, 1H, J=6.5 Hz).

EXAMPLE 3

Synthesis of 3',5'-disuccinyl-5-fluoro-2'-deoxyuridine

To a solution of 500 mg (2.02 mmole) of 5-fluoro-2'-deoxyuridine in 6 ml of anhydrous pyridine was added 500 mg (5.00 mmole) of succine anhydride at room temperature, and the mixtue was stirred overnight. The reaction mixture was poured into 60 ml of ice-cold water and stirred for 1 hour. To the mixture was added 2N HCl to adjust to pH 4.00, and the solution was extracted three times with 30 ml of ethyl acetate. The extracts were concentrated at room temperature under reduced pressure to obtain crude product. The crude product was dissolved in chloroform and subjected to column chromatography on silica gel. The fractions eluted at the chloroform-ethanol ratio of 90:10 to 85:15 were collected and given to give 3',5'-disuccinyl-5-fluoro-2'-deoxyuridine. The yield was 80%.

UV(λmax): 209 nm, 268 nm

NMR($\delta_{D3COD}^{TMS}$): 2.5–2.7 (m, 10H), 4.2–4.4 (m, 3H), 5.2–5.4 (n, 1H), 6.25 (t, 1H), 7.92 (d, 1H, J=6.5 Hz).

m.p.: 116°–117° C.

EXAMPLE 4

Synthesis of 3',5'-bis-(β-carboxyundecanoyl)-5-fluoro-2'-deoxyuridine

A solution of 500 mg (2.02 mmol) of 5-fluoro-2'-deoxyuridine and 12.2 mg (0.1 mmol) of 4-dimethylaminopyridine in 15 ml of anhydrous pyridine was prepared and 1,200 mg (5.0 mmole) of n-octyl succinic anhydride was added thereto at room temperature. The mixture was stirred at room temperature overnight. The reaction mixture was poured into 100 ml of ice water, and the mixture was stirred for 1 hour. To the mixture was added 2N HCl to adjust to pH 4.0, and the solution was extracted three times with 50 ml of chloroform. The extracts were concentrated at room temperature under reduced pressure to obtain crude product, and the product was dissolved in chloroform. The solution was passed through a column chromatography on silica gel and the eluates obtained at the chloroform-ethanol ratio ranging from 100:0 to 97:3 were collected and concentrated to give 3',5'-bis-(β-carboxyundecanoyl)-5-fluoro-2'-deoxyuridine. The yield was 85%.

UV(λmax): 209 nm, 268 nm

NMR($\delta_{CDCl3}^{TMC}$): 0.85 (t, 6H), 1.3 (s, 28H), 2.1–2.9 (m, 8H), 4.2–4,4 (m, 3H), 5.1–5.2 (m, 1H), 6.15 (t, 1H), 7.9 (d, 1H, J=6.5 Hz).

EXAMPLE 5

Synthesis of 3',5'-bis-(β-carboxytridecanoyl)-5-fluoro-2'-deoxyuridine

A solution was first prepared by dissolving 500 mg (2.02 mmole) of 5-fluoro-2'-deoxyuridine and 12.2 mg (0.1 mmole) of 4-dimethylaminopyridine in 15 ml of anhydrous pyridine, and to the solution was added 1,340 mg (5.0 mmole) of n-decyl succinic anhydride at room temperature. The mixture was stirred at room temperature overnight. The reaction mixture was poured into 100 ml of ice water and stirred for 1 hour. The reaction mixture was adjusted to pH 4.0 with 2N HCl and extracted three times with 50 ml of chloroform. The extracts were concentrated at room temperature under reduced pressure to obtain crude product. The product was dissolved in chloroform and subjected to column chromatography on silica gel. The fractions eluted at the chloroform-ethanol ratio ranging from 100:0 to 98.2 were collected and concentrated to obtain 3',5'-bis-(β-carboxytridecanoyl)-5-fluoro-2-deoxyuridine. The yield was 80%.

UV($\lambda_{max}^{EtOH}$): 209 nm, 268 nm

NMR($\delta_{CDCl3}^{TMS}$): 0.85 (t, 6H), 1.3 (s, 36H), 2.1–2.9 (m, 8H), 4.2–4.4 (m, 3H), 5.1–5.2 (m, 1H), 6.15 (t, 1H), 7.9 (d, 1H, J=6.5 Hz).

EXAMPLE 6

Synthesis of 3',5'-bis-(β-carboxypentadecanoyl)-5-fluoro-2'-deoxyuridine 500 mg (2.02 mmole) of 5-fluoro-2'-deoxyuridine and 12.2 mg (0.1 mmole) of 4-dimethylaminopyridine were dissolved in 15 ml of anhydrous pyridine and 1,480 mg (5.0 mmole) of n-dodecyl succinic anhydride was added to the solution at room temperature. The mixture was stirred overnight and then adjusted to pH 4.0 with 2N HCl. The mixture was extracted three times with 50 ml of chloroform. The extracts were concentrated at room temperature under reduced pressure to obtain crude product. The product was dissolved in chloroform and subjected to column chromatography on silica gel. The eluates obtained at the chloroform-ethanol ratio ranging from 100:0 to 98:2 were collected and concentrated to give 3',5'-bis-(β-carboxypentadecanoyl)-5-fluoro-2'-deoxyuridine in a 80% yield.

UV($\lambda_{max}^{EtOH}$): 209 nm, 268 nm

NMR($\delta_{CDCl3}^{TMS}$): 0.85 (t, 6H), 1.3 (s, 44H), 2.1–2.9 (m, 8H), 4.2–4.4 (m, 3H), 5.1–5.2 (n, 1H), 6.15 (t, 1H), 7.9 (d, 1H, J=6.5 Hz).

EXAMPLE 7

Synthesis of 3',5'-bis-(3-carboxy-3-methylpentanoyl)-5-fluoro-2'-deoxyuridine

To a solution of 500 mg (2.02 mmole) of 5-fluoro-2'-deoxyuridine and 12.2 mg (0.1 mmole) of 4-dimethylaminopyridine in 15 ml of anhydrous pyridine was added 710 mg (5.0 mmole) of 3,3-dimethylglutaric anhydride at room temperature. The mixture was stirred at room temperature overnight and then adjusted to pH 4.0 with 2N HCl. The mixture was extracted three times with 50 ml of ethyl acetate. Ethyl acetate was distilled away at room temperature under reduced pressure to obtained crude product. The product was dissolved in chloroform. This solution was subjected to column chromatography on silica gel and the eluates obtained at the chloroform-ethanol ratio of 100:1 to 95:5 were collected and concentrated to give 3',5'-bis-(3-carboxy-3-methylpentanoyl)-5-fluoro-2'-deoxyuridine. The yield was 90%.

UV($\lambda_{max}^{EtOH}$): 209 nm, 268 nm

NMR($\delta_{CDCl3}^{TMS}$): 1.12 (s, 12H), 1.9–2.5 (m, 10H), 4.2–4.4 (m, 3H), 5.1–5.2 (m, 1H), 6.2 (t. 1H), 7.9 (d, 1H, J=6.5 Hz).

EXAMPLE 8

Antitumor activity of 5-fluoro-2'-deoxyuridine derivatives (in intraperitoneal administration)

Experiments were made with the 5-fluoro-2'-deoxyuridine derivatives of this invention in order to know its antitumor effect against mouse leukemia cells L1210 in comparison with its parent compound 5-fluoro-2'-deoxyuridine and other known antitumor agents.

BDF$_1$ mice (male, 6-week-old, Ca 24 g, in groups of 5 mice), which were abdominally implanted with $10^5$ cells of mouse leukemia L1210, which had been collected after 7-day cultivation in other mice, were used in the experiments.

The respective agents were given to the experimental mice intraperitoneally once a day for 5 consecutive days starting 24 hours after the implantation of tumor cells.

The antitumor effect of the respective agents were indicated by the rate of increase in the length of the survival period obtained from the groups given the agents in contrast with the length of the survival period of the control group (not given the agents).

The dose, which is required to increase the lifespan of the experimental mice 30% as compared with the control group, is indicated by ILS$_{30}$ and the dose, which is required to effect the maximum increase of lifespan (Max. ILS(%)), is indicated by ILS max. ILS max./ILS$_{30}$ is to represent the therapeutic index which indicates the safety of the agents.

The results of the experiments are as shown in Table 1.

TABLE 1

| Compound | Antitumor activity | | | Therapeutic index (ILS max./ILS$_{30}$) |
|---|---|---|---|---|
| | ILS$_{30}$ (μmol · kg$^{-1}$ · day) | ILS max (μmol · kg$^{-1}$ · day) | Max. ILS (%) | |
| Compounds of this invention: | | | | |
| 3',5'-didecanoyl-5-fluoro-2'-deoxy-uridine | 18 | 180 | 52 | 10.0 |
| 3',5'-didodecanoyl-5-fluoro-2'-deoxy-uridine | 1.0 | 45 | 62 | 45.0 |
| 3',5'-ditetradecanoyl-5-fluoro-2'-deoxy-uridine | — | 4.5 | 61 | — |
| 3',5'-diadipoyl-5-fluoro-2'-deoxy-uridine | — | 20 | 58 | 20.0 |
| Compounds for comparison: | | | | |
| 5-fluoro-2'-deoxy-uridine | 200 | 400 | 54 | 2.0 |
| 3',5'-dihexanoyl-5-fluoro-2'-deoxy-uridine | 10 | 40 | 38 | 4.3 |
| 3',5'-dipalmitoyl-5-fluoro-2'-deoxy-uridine | 0.8 | 4.0 | 55 | 5.0 |

As seen from Table 1, the compounds of this invention display a strong antitumor effect in very small doses and also have a very good therapeutic index.

EXAMPLE 9

Antitumor activity of 5-fluoro-2'-deoxyuridine derivatives (in oral administration)

The antitumor effect of 3',5'-didecanoyl-5-fluoro-2'-deoxyuridine, 3',5'-didodecanoyl-5-fluoro-2'-deoxyuridine and 3',5'-ditetradecanoyl-5-fluoro-2-deoxyuridine selected from the compounds of this invention on mouse leukemia L1210 was examined as compared with their parent compound 5-fluoro-2'-deoxyuridine and also with 3',5'-diotanoyl-5-fluoro-2'-deoxyuridine.

BDF, mice (male, 6-week-oil, Ca 24 g in groups of 5 mice), which were abdominally implanted with $1 \times 10^5$ cells of mouse leukemia L1210, which had been collected after 7-day cultivation in other mice, were used as experimental animals.

The respective agents were administered orally three times, i.e. on the first day, third day, and fifth day, starting 24 hours after the implantation of tumor cells.

The antitumor effect of the respective agents were indicated by the rate of increase in the length of the survival period obtained from the groups given the agents against the length of the survival period of the control group (not given the agents).

The results are shown in Table 2. As seen from Table 2, 3',5'-didecanoyl-5-fluoro-2'-deoxyuridine, 3',5'-didodecanoyl-5-fluoro-2'-deoxyuridine, and 3',5'-ditetradecanoyl-5-fluoro-2'-deoxyuridine which are included in the compounds of this invention showed much higher antitumor effect also in oral administration as compared with their parent compound, 5-fluoro-2'-deoxyuridine, and 3',5'-2-dioctanoyl-5-fluoro-2'-deoxyuridine.

TABLE 2

| Compound | Dose (mg/kg/day) | ILS (%) | Change in body weight (1–4 d, g/mouse) |
|---|---|---|---|
| Compounds of this invention: | | | |
| 3',5'-didecanoyl-5-fluoro-2'-deoxyuridine | 10 | 7 | −0.8 |
| | 30 | 26 | −1.4 |
| | 100 | 15 | −2.4 |
| | 300 | 20 | −3.8 |
| 3',5'-didodecanoyl-5-fluoro-2'-deoxyuridine | 10 | 0 | +1.0 |
| | 30 | 5 | +1.0 |
| | 100 | 15 | 0 |
| | 300 | 40 | −2.6 |
| 3',5'-tetradecanoyl-5-fluoro-2'-deoxyuridine | 1 | 3 | +2.2 |
| | 3 | 3 | +2.0 |
| | 10 | 27 | −0.8 |
| | 30 | 33 | −1.4 |
| | 100 | 17 | −2.4 |
| Compounds for comparison: | | | |
| 5-fluoro-2'-deoxyuridine | 10 | 15 | +0.6 |
| | 30 | 10 | +1.8 |
| | 100 | 15 | −4.2 |
| | 300 | 10 | −5.2 |
| 3',5'-dioctanoyl-5-fluoro-2'-deoxyuridine | 10 | −5 | +1.8 |
| | 30 | 3 | +1.6 |
| | 100 | −5 | −2.8 |
| | 300 | 5 | −2.2 |
| Control | — | 0 | +0.4 |

EXAMPLE 10

Rate of hydrolysis of 5-fluoro-2'-deoxyuridine derivatives by esterase

Experiments were made on the 5-fluoro-2'-deoxyuridine derivative of this invention to determine the rates of releasing its parent compount (5-fluoro-2'-deoxyuridine) in the enzymatic hydrolysis conducted by use of estrase extracted from the porcine liver.

A 10 μg/ml isotonic solution of the experimental compound in a phosphate buffer (pH 7.00) was prepared and the estrase (manufactured by Sigma) extracted from the porcine liver was added to the solution at 37° C. in such a way as to provide the enzyme concentration ranging from 0.03 units/ml to 150 units/ml. Then the sample (10 μl) was injected into an HPLC column periodically to determine the amount of 5-fluoro-2'-deoxyuridine release by the enzyme reaction.

The time (t½) required for ½ the amount of the 5-fluoro-2'-deoxyuridine derivative, which was used in the hydrolysis, to be converted into its parent compound at the respective concentrations of the enzyme is shown as the index to indicate the rate of hydrolysis.

The results are as shown in Table 3.

TABLE 3

| Compound | Enzyme concentration (units/ml) | t½ (min) |
|---|---|---|
| Compounds of this invention: | | |
| 3',5'-didecanoyl-5-fluoro-2'-deoxyuridine | 0.3 | 140 |
| | 0.6 | 72 |
| 3',5'-didodecanoyl-5-fluoro-2'-deoxyuridine | 150.0 | 4000 |
| 3',5'-diadipoyl-5-fluoro-2'-deoxyuridine | 6.0 | 438.7 |
| | 12.0 | 216.5 |
| 3',5'-diglutaryl-5-fluoro-2'-deoxyuridine | 150.0 | 437.2 |
| 3',5'-disuccinyl-5-fluoro-2'-deoxyuridine | 150.0 | 3224.0 |
| Compounds for comparison: | | |
| 3',5'-dipropanoyl-5-fluoro-2'-deoxyuridine | 3.0 | 47.4 |
| | 6.0 | 24.2 |
| 3',5'-dibutyryl-5-fluoro-2'-deoxyuridine | 0.75 | 42.4 |
| | 1.50 | 21.7 |
| 3',5'-dihexanoyl-5-fluoro-2'-deoxyuridine | 0.045 | 32.5 |
| | 0.075 | 24.0 |
| | 0.15 | 10.0 |
| 3',5'-dioctanoyl-5-fluoro-2'-deoxyuridine | 0.03 | 18.2 |
| | 0.045 | 15.6 |

As shown in Table 3, the understanding that the compounds of this invention release their parent compound (5-fluoro-2'-deoxyuridine) at a very slow rate in the enzymatic reaction and that they have a property to slowly release 5-fluoro-2'-deoxyuridine in the enzyme system in vivo after their administration in the living body can be well supported.

EXAMPLE 11

Behavior to release FUdR from the compound due to the enzyme system in the plasma The release rates of 5-fluoro-2'-deoxyuridine (FUdR) from the compound of this invention at 37° C. in the rat plasma (20%), diluted with 0.1M phosphate buffer, pH 7.0, were measured.

The compound of this invention was added to the plasma diluted with an isotonic solution of phosphate buffer to a concentration of 4×10⁻⁵M (corresponding to FUdR 9.85 μg/ml) and was incubated at 37° C. The sample (10 μl) was injected into an HPLC column periodically to determine the amount (μg/ml) of 5-fluoro-2'-deoxyuridine released by the enzymatic reaction.

The results are as shown in Table 4.

As seen from Table 4, it is clear that the compounds of this invention release their parent compound at a very slow rate in the rat plasma as compared with 3',5'-dihexanoyl-5-fluoro-2'-deoxyuridine and 3',5'-dioctanoyl-5-fluoro-2'-deoxyuridine and that they have a property to release 5-fluoro-2'-deoxyuridine slowly in vivo after their administration into the living body.

TABLE 4

| | Release rate of 5-fluoro-2'-deoxyuridine (μg/ml) | | | | |
|---|---|---|---|---|---|
| Compound | after 100 min | after 200 min | after 300 min | after 400 min | after 500 min |
| Compounds of this invention: | | | | | |
| 3',5'-didecanoyl-5-fluoro-2'-deoxyuridine | 4.7 | 6.7 | 7.8 | 8.5 | 9.3 |

TABLE 4-continued

| | Release rate of 5-fluoro-2'-deoxyuridine (μg/ml) | | | | |
|---|---|---|---|---|---|
| Compound | after 100 min | after 200 min | after 300 min | after 400 min | after 500 min |
| 3',5'-didodecanoyl-5-fluoro-2'-deoxyuridine | 1.2 | 2.2 | 2.9 | 3.8 | 4.2 |
| Compounds for comparison: | | | | | |
| 3',5'-dihexanoyl-5-fluoro-2'-deoxyuridine | 7.8 | 9.85 | — | — | — |
| 3',5'-dioctanoyl-5-fluoro-2'-deoxyuridine | 9.85 | — | — | — | — |

EXAMPLE 12

Preparation of injections

The compound (3',5'-dimyristoyl-5-fluoro-2'-deoxyuridine) of this invention and 0.5–1% polyoxyethylene hardened castor oil were dissolved in an aqueous solution (pH 6.00–7.50) to obtain an injection containing 0.3 mg–1 mg/ml of the compound.

EXAMPLE 13

Preparation of tables

Tablets of the following composition were prepared according to the ordinary method of forming tablets.

| Compound of this invention | |
|---|---|
| (3',5'-didodecanoyl-5-fluoro-2'-deoxyuridine) | 50 mg |
| Lactose | 50 mg |
| Corn starch | 40 mg |
| Calcium carboxymethyl cellulose | 57 mg |
| Magnesium stearate | 3 mg |
| Total | 200 mg |

EXAMPLE 14

Preparation of capsules

Hard gelatin capsules having the following composition per capsule were prepared according to the ordinary method of filling capsules.

| Compound of this invention | |
|---|---|
| (3',5'-ditetradecanoyl-5-fluoro-2'-deoxyuridine) | 10 mg |
| Lactose | 120 mg |
| Crystalline cellulose | 67 mg |
| Magnesium stearate | 3 mg |
| Total | 200 mg |

EXAMPLE 15

Preparation of liposomes

Liposomes preparation were obtained according to the ordinary method under ultrasonic treatment by use of an isotonic sodium chloride solution containing 26 mg of lecithin, 5 mg of cholesterol, and 40 mg of a compound (3',5'-didodecanoyl-5-fluoro-2'-deoxyuridine) of this invention.

Industrial Applications

The 5-fluoro-2'-deoxyuridine derivatives of this invention exhibit the antitumor effect of high level in low dose, provide an extremely remarkable safety, and have an excellent property of sustained releasing effect in vivo of 5-fluoro-2'-deoxyuridine. They are accordingly very useful as the remedy for malignant tumors.

We claim:

1. The 5-fluoro-2'-deoxyuridine derivative expressed by the following formula (I')
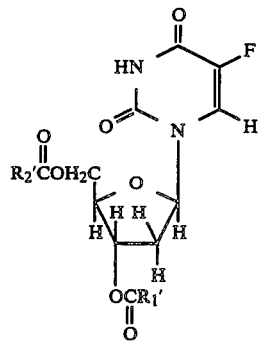
wherein $R_1'$ and $R_2'$ are the same or different from each other, each representing an alkyl group of 1 to 18 carbon atoms having a carboxyl group as substituent, or its pharmacalogically acceptable salt.
* * * * *